(12) United States Patent
Leone, Jr.

(10) Patent No.: US 6,302,890 B1
(45) Date of Patent: Oct. 16, 2001

(54) PELVIC ALIGNMENT ASSEMBLY

(75) Inventor: William Leone, Jr., Lighthouse Point, FL (US)

(73) Assignee: Leone Innovations Corporation, Lighthouse Point, FL (US)

( * ) Notice: Subject to any disclaimer, the term of this patent is extended or adjusted under 35 U.S.C. 154(b) by 0 days.

(21) Appl. No.: 09/526,896

(22) Filed: Mar. 16, 2000

(51) Int. Cl.$^7$ ................................................. A61B 17/58
(52) U.S. Cl. .............................................. 606/91; 606/99
(58) Field of Search .................................. 606/91, 99, 53, 606/81, 86, 92, 100, 102, 105; 623/22.12

(56) References Cited

U.S. PATENT DOCUMENTS

| | | | |
|---|---|---|---|
| 5,112,331 | * 5/1992 | Miletich | 606/53 |
| 5,122,145 | * 6/1992 | Fishbane | 606/102 |
| 5,603,717 | * 2/1997 | Benson | 606/102 |
| 5,616,147 | * 4/1997 | Gadelius | 606/102 |
| 5,700,268 | * 12/1997 | Bertin | 606/102 |
| 6,165,177 | * 12/2000 | Wilson et al. | 606/100 |
| 6,193,724 | * 2/2001 | Chan | 606/102 |

\* cited by examiner

Primary Examiner—Pedro Philogene

(74) Attorney, Agent, or Firm—Malloy & Malloy, P.A.

(57) ABSTRACT

A pelvic alignment assembly and method for its use during a total hip replacement surgery in order to accurately re-position the patient's pelvis in a true anterior-posterior or true lateral position so as to optimize the accurate positioning of a prosthetic acetabular cup into the patient's hip joint socket. The assembly includes an elongated pin having one end anchored to the pelvis of the patient and a base removably supported and attached to the opposite, outwardly extending end of the pin. The assembly also includes a mounting member movably connected to the base in a manner which enables the selective adjustment of the relative positions of the base and mounting member in order to dispose a level structure, fixedly secured to the base and movable therewith, into a horizontal position or other predetermined reference orientation. A locking assembly is mounted on the base so as to removably fix the position between the base and the mounting member and maintain the level structure in the predetermined orientation so that the base and mounting member can be removed from the pin. Prior to implanting the acetabular cup into the pelvis, the base, mounting member and level structure are repositioned on the pin and the patient is physically manipulated so as to re-orient the level structure back into the predetermined orientation thereby providing visual indication to the surgeon that the pelvis is re-oriented in the true anterior-posterior or true lateral position.

26 Claims, 3 Drawing Sheets

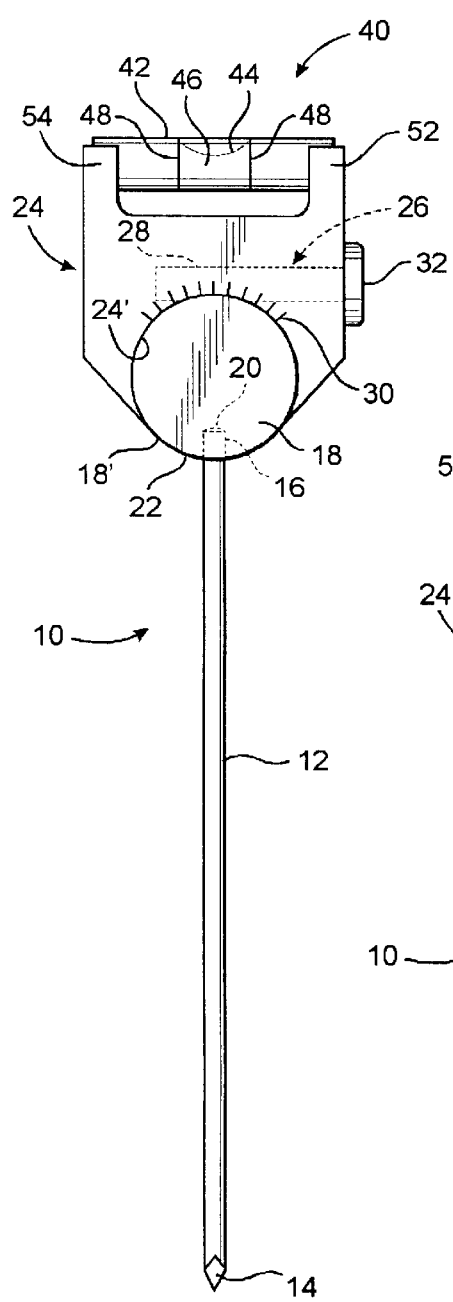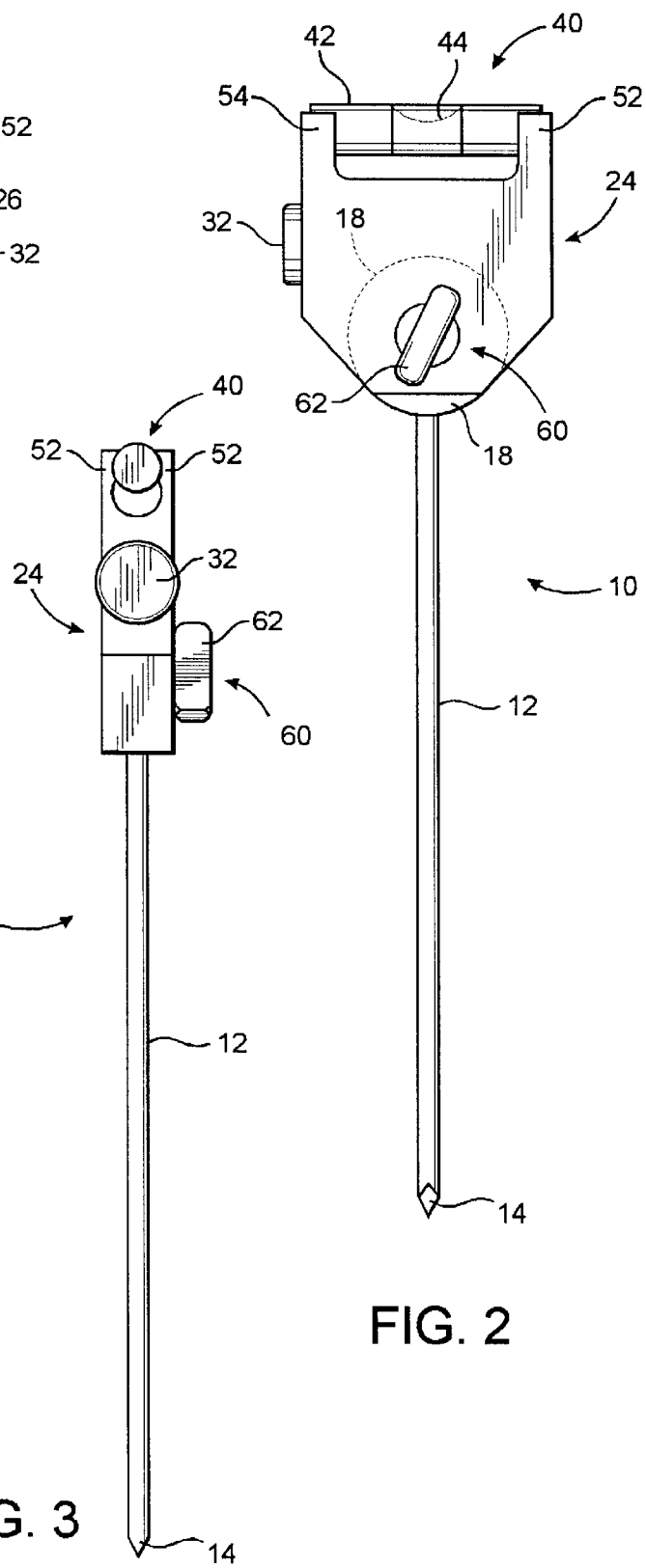
FIG. 1  FIG. 3  FIG. 2

PELVIC ALIGNMENT ASSEMBLY

BACKGROUND OF THE INVENTION

1. Field of the Invention

This invention is directed to a pelvic alignment assembly designed to be used during a total hip replacement surgery for purposes of accurately positioning a prosthetic acetabular cup in the hip joint socket by reproducing precise anatomical alignment of the pelvis. More in particular, immediately prior to the insertion of the acetabular cup, a surgeon utilizing the pelvic alignment assembly of the present invention can re-position the patient, typically by forward or backward rotation of the patient, and determine when the pelvis has accurately assumed a pre-determined "baseline" or reference position, initially established at the beginning of the surgical procedure, which is substantially indicative of a true lateral position or a true anterior-posterior position of the pelvis, and thereby, optimize the accurate positioning of the acetabular cup within patient's the hip joint socket.

2. Description of the Related Art

As people age, it is relatively common for there to be some deterioration of the hip joint, and more in particular, of the head of the femur or thigh bone, with the result often being that many such persons will have to undergo a total hip replacement ("THR") surgery performed by an orthopedic surgeon. A total hip replacement surgery involves the use of a prosthetic femoral component comprised of a stem that fits into the upper femur. On the upper or proximal aspect of the stem is a ball which will function to replace the patient's damaged or worn out femoral head. To accommodate placement and positioning of the femoral component within the hip joint, it is necessary to insert a prosthetic acetabular cup to receive the ball-like end of the femoral component in substitution for the socket of the human hip joint. In order to achieve optimum performance of these cooperative prosthetic components, the acetabular cup must be positioned as accurately as possible within the pelvis of the patient. Inaccurate positioning or alignment of the acetabular cup within the hip joint can present extensive and serious problems to the patient after surgery and the requisite healing period, such as providing the patient with a decreased range of motion, the subsequent and possibly accelerated loosening or failure of either or both of the acetabular and femoral components, as well as possible dislocation of the hip joint. Following surgery and progressively over the first year subsequent to surgery, scar tissue normally forms about the inserted prosthetic components, which serves to recreate a hip joint capsule called a pseudocapsule which typically aids in the prevention of hip dislocation. However, when the acetabular cup is oriented in a less than an optimal angular position, hip dislocation is thought to be much more likely even when the patient is performing normal, everyday activities which require the hip joint to pass through a normal range of motion. Hip dislocation is one of the most dreaded complications after THR surgery and it is quite well understood in the medical profession that the most common reason for post-operative total hip dislocation is less than optimally positioned acetabular components, also known as acetabular malposition.

In properly orienting the acetabular cup for receipt of the prosthetic femoral component, it is necessary to accurately establish both the abduction angle as well as the anteversion angle. Typically, the anteversion angle, also known as forward flexion, is generally in the range of about 10 degrees to about 25 degrees. The abduction angle is typically in the range of about 35 degrees to 50 degrees, with a most preferred angle being at or about 45 degrees. Due to the well recognized fact that an improperly positioned acetabular component can subsequently cause the patient numerous problems, as set forth above, a number of devices or instruments have been designed to aid in the proper positioning and/or alignment of the acetabular cup. These known devices have included cup positioners which comprise a pusher ball that is sized and shaped to fit the recess formed within the acetabular component, along with one or more positioned arms, a positioned flange juxtaposed to the pusher ball and a pusher arm connected to the ball and to the flange, to enable the user to push the acetabular cup, when it is resting on the flange into the patient's prepared acetabulum during the THR surgery. However, in the utilization of such devices, the pelvis of the patient should have been properly oriented in either a true anterior-posterior or a true lateral position in order to accomplish an optimal, predicted cup position. There has been, unfortunately, almost a complete lack of devices in the medical field to help with accurately achieving an established pelvic position, and this has left the surgeon to estimating, to the best of his or her ability, the position or alignment of the pelvis in order to utilize the known devices or instruments, discussed above, for positioning of the prosthetic acetabular cup within the hip joint. Estimation of the pelvic position, in the manner set forth above, frequently involves only the surgeon's visual observation of the patient's orientation in an effort to accomplish the desired pelvic alignment. It is further encumbered by so little of the patient's body being exposed during surgery because of the sterile surgical drapes covering the patient. As such, it is not uncommon to misjudge the anatomical alignment of the pelvis, particularly where the patient suffers from obesity, congenital abnormalities, or bone and/or soft tissue destruction from previous surgeries. In addition, there are close tolerances involved in accurately establishing both the anteversion angle and the abduction angle, discussed above. Therefore, the use of known devices of the type set forth above, or the unintentional failure to accurately determine the anatomical alignment of the pelvis in a true anterior-posterior or true lateral position, may very well result in the acetabular component being improperly positioned when implanted into the pelvis of the patient.

As such, there is a long felt need in the art for reliable, medical instrumentation which would be capable of accurately establishing a proper or preferred anatomical position of a patient's pelvis, which may be defined to mean a true anterior-posterior position or a true lateral position of the pelvis during a THR surgery. More in particular, prior to the implantation of the acetabular cup into the patient's pelvis, the pelvis should be repositioned into a predetermined position in order to optimally implant and orient the acetabular component related to the prosthetic femoral component, which as discussed above, can reproducibly only be accomplished if the pelvis of the patient is properly oriented in either a true anterior-posterior or a true lateral position. If an alignment assembly were developed to properly re-orient the patient in such a position, it would greatly enhance the surgeon's ability to optimally and reproducibly position the acetabular cup, and thereby, be more likely to result in the patient's being able to function through a normal range of movement, with a greatly decreased fear of either hip dislocation or accelerated deterioration of the implanted prosthetic components. If any such alignment assembly were developed, it would preferably include a visually observable instrument structured to facilitate the establishment and/or re-establishment of a baseline or reference position of the pelvis, when in its normal or proper anatomical alignment defined by a true anterior-posterior position or true lateral position. More specifically, any such alignment assembly should be structured so as to be capable of being adjustably oriented or positioned to reestablish the aforementioned baseline or reference position, indicative of proper pelvic alignment of the patient, and thereby, to more reliably assure the accurate placement of the acetabular cup.

SUMMARY OF THE INVENTION

The present invention is designed to address these and other needs which remain in the art and comprises an alignment assembly. The alignment assembly of the present invention is designed to assist with the accurate positioning of a prosthetic acetabular cup into the pelvis of a patient during a total hip replacement ("THR") surgery. More specifically, the alignment assembly of the present invention allows the surgeon to accurately orient the pelvis by repositioning the patient's pelvis into a previously established or baseline position of proper anatomical alignment for the accurate placement of the acetabular cup, and more in particular, wherein the patient is positioned in either a true anterior-posterior or a true lateral position, depending on the surgical approach which the surgeon elects to use.

The alignment assembly of the present invention comprises an elongated pin such as, but not limited to, a Steinmann pin. The distal end of the elongated pin is specifically structured to be anchored into the pelvis so as to extend outwardly therefrom. The alignment assembly further comprises a base removably mounted on the opposite, outwardly extending, proximal end of the elongated pin, with the base being movably connected to a mounting member. The mounting member includes a socket dimensioned and configured to removably receive the outwardly extending, proximal end of the elongated pin therein, so as to allow stable but removable support and attachment of the base to the elongated pin.

The alignment assembly additionally comprises an adjustment assembly, which is mounted at least in part on the base and which is at least partially interconnected to the mounting member. The adjustment assembly is specifically designed to be accessed from the exterior of the base, and more specifically, to be manipulated by the surgeon or other medical personnel, so as to selectively adjust the relative position between the base and the mounting member, as will be explained in greater detail hereinafter.

The alignment assembly additionally includes a visually observable instrument structured to facilitate the establishment and/or re-establishment of a baseline or reference position of the patient's pelvis in normal or proper anatomical alignment defined by a true anterior-posterior position or true lateral position. The visually observable instrument preferably comprises a level structure that is ideally, but not necessarily, in the form of a "bubble-type" of level secured to the base and moveable therewith. Further, the level structure is disposed on the base in a position which is readily observable by the surgeon and/or other medical personnel in attendance during periods of the surgical procedure, while the base is supported on the proximal end of the pin due to the interconnecting disposition of the mounting member, as generally set forth above.

In addition, the base of the alignment assembly preferably includes a locking assembly that is operatively connected to the mounting member as well as the base in a manner which is capable of being selectively positioned in either a locked or an unlocked position. The locked position prevents or significantly restricts movement between the base and the mounting member, thereby preventing operation of the adjustment assembly for purposes of changing the position of the base relative to the mounting member. With the locking assembly disposed in the locked position, the surgeon is reasonably assured that the intended position of the level structure relative to the elongated pin may be re-established, when necessary to accomplish the predetermined established anatomical alignment of the pelvis, immediately prior to insertion of the acetabular cup. Further, proper use and observation of the level structure allows the surgeon to re-establish the required pelvic alignment through minimal physical manipulation or repositioning of the patient, immediately prior to the insertion of the acetabular cup into the pelvis.

Use of the alignment assembly of the present invention during a THR surgery involves positioning the patient into a true anterior-posterior or true lateral position on the operating table. After appropriate preparation and draping of the patient, the distal end of the elongated Steinmann pin is anchored to the iliac crest of the patient's pelvis. Initial alignment of the pelvis is accomplished by orienting the elongated pin in an approximately perpendicular relation to the floor, ground or other supporting surface. The base, being movably connected to the mounting member, is supported on the pin by attaching the mounting member to the outwardly extending or proximal end of the pin. While the base remains supported on the pin, the adjustment assembly is manipulated by the surgeon or other medical personnel until the level structure, fixedly secured to the base and movable therewith, indicates that it is oriented into a true horizontal or other applicable reference position. The locking assembly is then manipulated into the locked position, thereby assuring a relative fixed orientation of the level structure relative to the pin, when the base is mounted thereon. The base, along with the mounting member and the level structure, can then be removed from the outwardly extending end of the pin, while the distal end of the pin remains anchored into the pelvis. The surgical procedure associated with a total hip replacement or THR then proceeds to the point where the acetabular cup is ready for insertion into the hip joint socket of the pelvis. Immediately prior to the insertion of the acetabular cup, the base is again supported on the elongated pin by reattaching the mounting member to the proximal end. The locking assembly still maintains the level in its previously, predetermined fixed position relative to the pin. Accordingly, in order to re-orient or position the level structure into the true horizontal or established reference orientation, which was established by locking the mounting member to the base, the patient is then physically moved, such as by rotating the patient, preferably forward or backward, to once again orient the level structure in the predetermined, initially established baseline or reference position. Visual observation of the level structure indicates to the surgeon or other medical personnel, such as when the preferred "bubble" is appropriately located or "centered" within the level structure, that the level structure, the elongated pin and accordingly, the pelvis is re-oriented in the same, pre-determined established anatomical alignment for optimizing the accurate positioning and insertion of acetabular cup.

The objects and features of the present invention set forth above are intended to be illustrative only and should not be construed as limiting in any way. In fact, these and other objects, features and advantages associated with the present invention should become more evident from the drawings and the detailed description of the preferred embodiments for the invention, which follow.

BRIEF DESCRIPTION OF THE DRAWINGS

For a fuller understanding of the nature of the present invention, reference should be made to the following detailed description taken in connection with the accompanying drawings in which:

FIG. 1 is a front view of the alignment assembly of the present invention.

FIG. 2 is a side view of the alignment assembly illustrated in FIG. 1.

FIG. 3 is a rear view of the alignment assembly illustrated in FIGS. 1 and 2.

Like reference numerals refer to like parts throughout the several views of the drawings.

DETAILED DESCRIPTION OF THE PREFERRED EMBODIMENT

Figure 4:
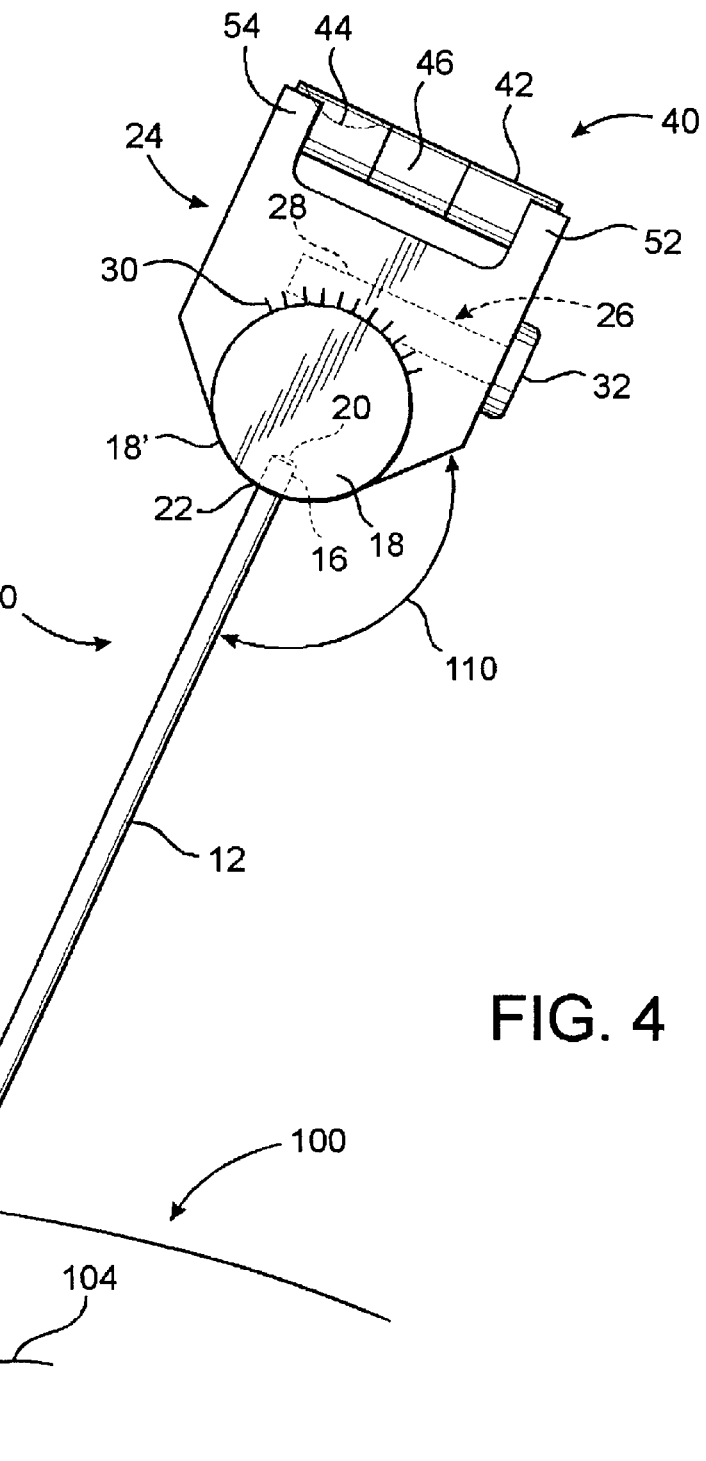
FIG. 4 is a front view of the alignment assembly of the present invention as initially inserted in predetermined relation to the pelvis of a patient involved in a total hip replacement (THR) surgery.

As shown in the accompanying Figures, the present invention is directed to an alignment assembly designed generally for use in a total hip replacement (THR) surgery, and more specifically, is structured to optimize the positioning and orientation of a prosthetic acetabular cup into the pelvis of a patient during THR surgery. More specifically, the alignment assembly allows a surgeon or other medical personnel to establish a baseline or reference position of the patient, when the pelvis is disposed in an accurate, anatomically aligned position, thereby facilitating accurate placement of the acetabular component into the pelvis during the THR. As will be explained in greater detail hereinafter, the pelvic alignment assembly of the present invention allows the surgeon or other medical personnel to orient the patient's pelvis and establish a predetermined, "baseline" or reference position at the beginning of a THR surgery, and to subsequently determine that baseline reference orientation and re-establish it by physical manipulation of the patient immediately prior to the insertion of the acetabular cup into the patient's pelvis.

With reference to FIGS. 1 through 5, the alignment assembly of the present invention is shown in assembled formed and is generally indicated by reference numeral 10. The alignment assembly 10 includes an elongated pin 12, which may comprise a type of pin well known in the medical field as a Steinmann pin. The elongated pin 12 has a distal end 14 which is preferably threaded, sharpened, or otherwise structured to facilitate its being anchored into the pelvis of a patient during a THR surgical procedure. The opposite or proximal end 16 of the elongated pin 12 is rounded, blunted or otherwise structured for removable support and attachment to a mounting member 18. Attachment of the mounting member 18 to the proximal end 16 of pin 12 is preferably accomplished through the provision of a socket or like structure 20, having an open end 22, wherein the socket 20 and the open end 22 are both disposed and dimensioned to receive the proximal end 16 of pin 12 on the interior of the mounting member 18 in a manner which facilitates the stable but removable support of the mounting member 18 thereon.

The alignment assembly of the present invention also comprises a housing or base, generally indicated as 24, which is movably connected to the mounting member 18, such that the relative positions between the base 24 and the mounting member 18 can be selectively varied, for reasons to be explained in greater detail hereinafter. As best shown in FIG. 1, the mounting member 18 preferably has a curved and/or at least partially circular configuration, such that a portion of the periphery 18' of the mounting member 18 is at least partially enclosed or otherwise disposed in immediately adjacent relation to an interior recess 24' or like receiving portion of the mounting member 24. The recess 24' is cooperatively configured and structured with the mounting member 18 so as to facilitate a stable but adjustably movable connection therebetween. Due to the fact that the mounting member 18 and the base 24 are relatively movable, the open end 22 of the receiving socket 20 is disposed on an exposed portion of the periphery 18' of mounting member 18. Accordingly, regardless of the relative orientations of the mounting member 18 or the base 24, the open end 22 of socket 20 will nearly always be exposed, so as to allow insertion or removal of the proximal end 16 of the elongated pin 12.

Figure 5:
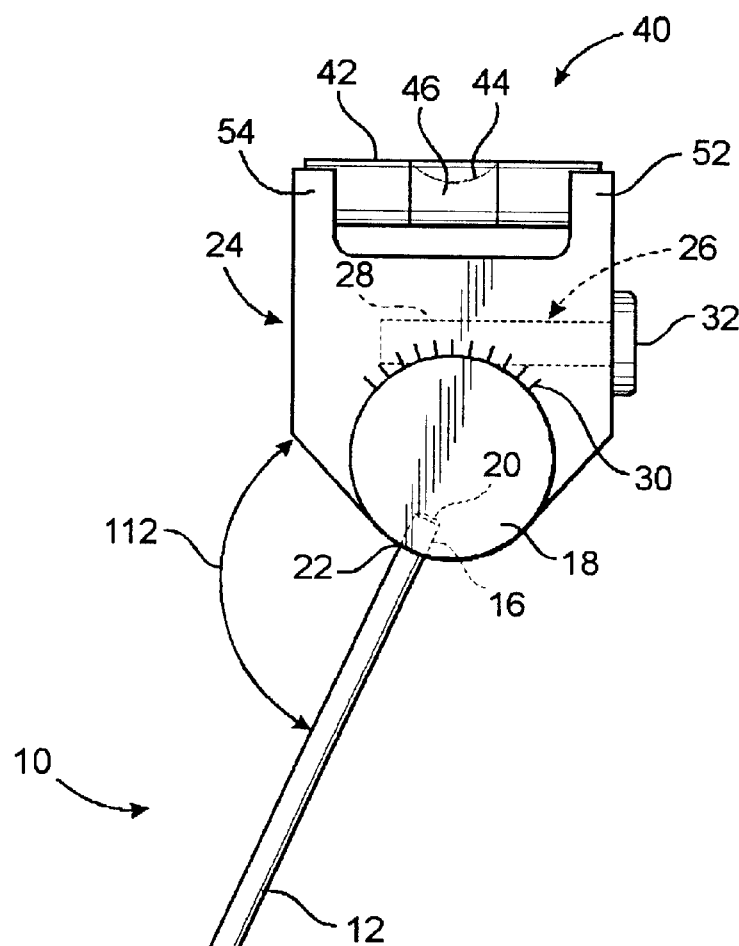
FIG. 5 is a front view of the alignment assembly of the present invention with the housing positioned and locked into a horizontal orientation indicated by a bubble of the associated level being disposed in a centered position, and thereby defining a reference or baseline position of an anatomically aligned pelvis.

The alignment assembly of the present invention also comprises a adjustment assembly, generally indicated as 26 in FIGS. 1, 4 and 5. The adjustment assembly is mounted, at least in part, on the base 24 and is structured to accurately adjust the positioning of the base 24 relative to the mounting member 18. The adjustment assembly 26 may include a drive gear represented in phantom lines in FIG. 1 and indicated as 28. In addition, the adjustment assembly 26 includes a driven gear 30 formed at least in part on the mounting member 18 and disposed in mating engagement with the drive gear 28. The driven gear 30 may be more accurately represented as a gear segment extending along the periphery 18' or other portion of the mounting member 18, generally on the interior of the base 24, so as to be accurately disposed in mating engagement with the elongated drive gear 28. It should be emphasized that the aforementioned gear assembly, including drive gear 28 and driven gear or gear segment 30, could take a variety of different structural configurations, other than that shown in FIGS. 1, 4, and 5, in order to accomplish the selective and accurate orientation of the base 24 relative to the mounting member 18. The adjustment assembly 26 also includes a control portion 32, preferably in the form of a knob being exteriorly accessible on the base 24 and connected to the drive gear 28 so as to rotate therewith. The disposition and dimension of the control knob 32 is such as to be easily manipulated by the surgeon or other medical personnel during the surgical procedure in a manner which will not distract the surgeon or interfere with the surgical procedure. As will be explained in greater detail with reference to FIGS. 4 and 5, manipulation of the control knob 32 will allow the surgeon or other medical personnel to position the base 24 relative to the mounting member 18 and into a preferred orientation.

The alignment assembly of the present invention also comprises a visually observable instrument, such as a level structure, generally indicated as 40 throughout the various Figures. In the embodiment shown, the level structure 40 comprises a "bubble" level having a sealed outer casing 42, partially filled with a liquid and specifically structured to include an air or gas bubble 44, which freely travels along the interior of the casing 42 dependent on the orientation of the casing 42. With reference to FIGS. 1, 3 and 5, the bubble is shown in a center position 46, as can be readily determined by the existence of spaced apart markings 48 formed on the sealed casing 42 and correspondingly disposed and dimensioned relative to one another to accurately align with the length and/or position of the bubble 44, when the casing 42 is in a true horizontal position. As shown in FIG. 4, orientation of the casing 42 of level 40 in an angular position, other than true horizontal, serves to automatically position the bubble 44 out of alignment with the center position 46, such as at one end of casing 42.

The level structure 40 is preferably fixedly secured to the base 24 so as to be movable therewith. For example, the upper end of the base 24 may include a cradle-like structure defined by two pairs of spaced apart arms 52, 52 (see FIG. 2) and 54, 54, each pair disposed at respective ends of the cradle-like structure. As such, the level structure 40 is disposed in a position which is clearly and easily observable by the surgeon or other medical personnel during the THR surgery. Accordingly, movement of the base 24 relative to the mounting member 18, preferably through manipulation of the control knob or portion 32 of the adjustment assembly 26, will cause repositioning or orientation of the level structure 40, due to the fact that it is secured to the base 24 so as to move therewith, as set forth above.

Another structural feature of the present invention is the incorporation of a locking assembly, generally indicated as 60 and best shown in FIGS. 2 and 3. The locking assembly 60 preferably includes a wing nut or like member 62, exteriorly protruding from a rear surface or other portion of the base 24. The wing nut or like member 62 may be interconnected to the mounting member 18 as well as to a portion of the base 24. Therefore, a "tightening" of the member 62 will accomplish a removable, locking engagement between the base 24 and the mounting member 18, so as to prevent relative movement therebetween, even during inadvertent attempts to rotate or otherwise manipulate the control knob 32. Therefore, the position of the base 24 and accordingly, of the level structure 40 relative to the mounting member 18 can be secured in order to establish a reference or baseline position of the mounting member 18, base 24 and level structure 40, relative to the elongated pin 12, which has been placed in the pelvis of the patient, as will be explained in greater detail hereinafter, primarily with reference to FIGS. 4 and 5.

Utilizing the alignment assembly 10 of the present invention, positioning of a prosthetic acetabular cup during a total hip replacement (THR) surgery is optimally positioned by accurately accomplishing proper anatomical alignment defined by a true anterior-posterior or true lateral position of the pelvis. Once the patient is properly oriented, as set forth above, the pelvic alignment assembly 10 is applied as best demonstrated in FIGS. 4 and 5. More specifically, the patient, generally indicated as 100, is appropriately prepared and draped as part of the normal surgical procedure. Subsequently, the elongated pin 12 which, as set forth above may be a Steinmann pin, is inserted into the patient 100 hip area, preferably at the site of a small incision 102. Upon insertion, the distal end 14 of the pin 12 is anchored into the pelvis of the patient, and more preferably, into the iliac crest schematically represented as 104. The pin 12 is preferably anchored in an orientation which is approximately perpendicular to the ground or other supporting surface or reference object. Once the pin 12 is appropriately anchored into the iliac crest 104, the base 24 is removably secured to the proximal end 16 of the pin 12, by inserting the proximal end 16 through the exposed open end 22 and receiving socket 20 of the mounting member 18, as shown in FIG. 4.

Upon initially mounting the base 24 on the proximal end 16 of the pin 12, the level structure 40 will most probably be oriented at an arbitrary angle, schematically indicated as 110. As shown in FIG. 5, the adjustment assembly 26 is then operated, through manipulation of the control knob 32, so as to dispose the level structure 40 into a predetermined alignment which is preferably defined by a horizontal orientation of the level structure. As set forth above, a horizontal orientation of the level 40 is capable of being easily determined by a visual indication that the bubble 44 is disposed within the center position 46, such as is shown in FIG. 5. The locking assembly 60 is then tightened through manipulation of the wing nut or other member 62, so as to prevent relative movement between the base 24 and level structure 40, and the mounting member 18 and pin 12, respectively. In this locked position, the base 24 and the level structure 40 will now be disposed at an angle 112 relative to pin 12 which differs from angle 100.

Once the locking assembly 60 has been tightened in the manner as set forth above, the base 24 can be removed from the proximal end 16 of pin 12, while the elongated pin 12 remains anchored in the pelvis 104 during the remainder of the surgical procedure or until the acetabular cup is implanted. Once the surgical procedure has proceeded to the point where the patient is ready for the insertion of the prosthetic acetabular cup, the base 24, still remaining in its locked position relative to the mounting member 18, is again mounted on the proximal end 16 of the elongated pin 12, by inserting the proximal end 16 through the open end 22 and into the interior of the receiving socket 20. The patient is then physically manipulated, normally by rotating the patient forward and backward, to once again orient the pin 12 and the level 40 into a position demonstrated in FIG. 5, wherein the bubble 44 is disposed into alignment with the center position 46. Once such alignment occurs, the surgeon is assured that the pelvis has been re-established in the proper, true anterior-posterior or true lateral position. The acetabular cup can then be inserted into the pelvis, with the pelvis being again disposed in the original reference or "baseline" position, initially established by originally orienting the level structure 40, at the beginning of the surgical procedure, as outlined above.

Since many modifications, variations and changes in detail can be made to the described preferred embodiment of the invention, it is intended that all matters in the foregoing description and shown in the accompanying drawings be interpreted as illustrative and not in a limiting sense. As one example only, other level structures aside from a bubble level could be utilized with the present invention, such as a laser level. Thus, the scope of the invention should be determined by the appended claims and their legal equivalents.

Now that the invention has been described,

What is claimed is:

1. An alignment assembly designed to aid with the accurate re-orientation of the pelvis of a patient during a surgical procedure, said alignment assembly comprising:
   a) an elongated pin terminating at a distal end and structured to be anchored to the patient's pelvis,
   b) a base including a level structure secured thereto in a position to facilitate visual observation thereof,
   c) a mounting member movably attached to said base and removably mounted on said pin in interconnecting, supporting relation between said pin and said level structure, and d) said level structure adjustably positionable relative to said pin into a predetermined aligned position indicative of a true anterior-posterior position or true lateral position of the pelvis.

2. An alignment assembly as recited in claim 1 wherein said pin comprises a linear configuration and further includes a proximal end oppositely disposed to said distal end and configured to removably support said mounting member thereon.

3. An alignment assembly as recited in claim 2 wherein said mounting member comprises a socket having an open end formed adjacent an exposed portion thereof, said socket extending inwardly into said mounting member.

4. An alignment assembly as recited in claim 3 wherein said open end is disposed substantially adjacent an outer periphery of said mounting member and said socket extends radially inward a sufficient depth to receive said proximal end therein in supporting relation to said mounting member and said base.

5. An alignment assembly as recited in claim 1 wherein said mounting member and said base are rotatably connected, said level structure fixedly secured to said base and movable therewith relative to said mounting member and said pin.

6. An alignment assembly as recited in claim 1 wherein said mounting member comprises a curvilinear peripheral portion at least partially disposed on an interior of said base, said base and said mounting member movable relative to one another along said peripheral portion.

7. An alignment assembly as recited in claim 6 wherein said mounting member comprises a substantially circular configuration at least a portion of which is disposed within said base; a socket formed within said mounting member and including an open end formed adjacent an exposed portion of said circular periphery.

8. An alignment assembly as recited in claim 7 wherein said pin comprises a linear configuration and further includes a proximal end oppositely disposed to said distal end and configured to be removably received within said socket through said open end in supporting engagement with said mounting member.

9. An alignment assembly as recited in claim 5 further comprising an adjustment assembly movably mounted in interconnecting relation between said mounting member and said base and including a control portion being at least partially accessible exteriorly of said base.

10. An alignment assembly as recited in claim 9 wherein said control portion is operable to vary the relative positions of said mounting member and said base so as to dispose said level structure into a horizontal position which defines said predetermined aligned position.

11. An alignment assembly as recited in claim 10 further comprising a locking assembly disposed in interconnecting relation between said mounting member and said base and structured to removably secure said mounting member and said base in fixed relation to one another.

12. An alignment assembly as recited in claim 1 further comprising an adjustment assembly movably mounted in interconnecting relation between said mounting member and said base and including a control portion being at least partially accessible exteriorly of said base.

13. An alignment assembly as recited in claim 12 wherein said control portion is operable to vary the relative positions of said mounting member and said base so as to dispose said level structure into a horizontal position which defines said predetermined aligned position.

14. An alignment assembly as recited in claim 13 further comprising a locking assembly disposed in interconnecting relation between said mounting member and said base and structured to removably secure said mounting member and said base in fixed relation to one another.

15. A method of re-aligning the pelvis in a predetermined orientation utilizing the alignment assembly of claim 1, said method comprising the steps of:

a) orienting the patient in a position which disposes the pelvis in a true anterior-posterior or true lateral position, b) inserting said pin into the patient in substantially perpendicular relation to a supporting surface, c) anchoring said distal end of said pin into the patient's pelvis in approximately perpendicular relation to the supporting surface, d) mounting said mounting member on said pin in supporting relation to said base and said level structure, e) adjusting the position of said level structure relative to said pin until said level structure is in a predetermined orientation indicative of a true anterior-posterior position or true lateral position of the pelvis, f) fixing the relative position between said pin and said level so as to establish a reference position of the patient indicative of the true anterior-posterior position or true lateral position of the pelvis, g) removing said mounting member and said base from said pin, h) continuing with the intended surgical procedure until it is necessary to re-position the pelvis in the true anterior-posterior position or true lateral position, i) remounting said mounting member and said base on said pin while maintaining a fixed position therebetween, and j) orienting the patient into the reference position and thereby dispose said level structure in the predetermined aligned position indicative of the normal anatomical alignment of the pelvis.

16. A method as recited in claim 15 comprising adjusting the position of said level structure relative to said pin into the predetermined orientation by disposing said level structure into a horizontal orientation.

17. A method as recited in claim 15 comprising anchoring said distal end of said pin into the patient's pelvis.

18. An assembly as recited in claim 17 comprising adjusting the position of said level structure relative to said pin by selectively adjusting the relative position between said mounting member and said base.

19. An assembly as recited in claim 18 comprising fixing the relative position between said pin and said level structure by removably locking the relative positions between said mounting member and said base.

20. An alignment assembly designed to accurately re-orient the pelvis of a patient during a surgical procedure, said alignment assembly comprising:

a) an elongated pin terminating at a distal end, said distal end structured to be anchored to the patient's pelvis, b) a base including a level secured thereto in a position to facilitate visual observation thereof, c) a mounting member movably attached to said base and removably mounted on said pin in interconnecting, supporting relation between said pin and said level, d) an adjustment assembly movably interconnected between said mounting member and said base, e) said adjustment assembly selectively operable to vary the relative position between said mounting member and said base and dispose said level into a horizontal position indicative of a true anterior-posterior position or true lateral position of the pelvis.

21. An alignment assembly as recited in claim 20 further comprising a locking assembly disposed in interconnecting relation between said mounting member and said base and structured to removably secure said mounting member and said base in fixed relation to one another.

22. An assembly as recited in claim 20 wherein said adjustment assembly comprises a control portion mounted exteriorly of said base and manually operable to vary the relative position of said mounting member and said base and thereby dispose said level into said horizontal position.

23. An alignment assembly as recited in claim 22 wherein said adjustment assembly comprises a gear assembly at least partially attached to both said base and said mounting member and operable to selectively vary the position therebetween.

24. An alignment assembly as recited in claim 23 wherein said gear assembly comprises a drive gear movably mounted on said base and a driven gear secured to said mounting member and disposed in mating engagement with said drive gear.

25. An alignment assembly as recited in claim 24 wherein said control portion comprises a knob mounted on an exterior of said base and fixedly secured to said drive gear.

26. An alignment assembly as recited in claim 20 wherein said level comprises a bubble level.

* * * * *